(12) United States Patent
Kaiser

(10) Patent No.: US 8,045,779 B2
(45) Date of Patent: Oct. 25, 2011

(54) METHOD AND DEVICE FOR EVALUATION OF AN IMAGE AND/OR OF A TIME SEQUENCE OF IMAGES OF TISSUE OR TISSUE SAMPLES

(75) Inventor: Werner A. Kaiser, Jena (DE)

(73) Assignee: Werner Kaiser, Jena (DE)

( * ) Notice: Subject to any disclaimer, the term of this patent is extended or adjusted under 35 U.S.C. 154(b) by 1056 days.

(21) Appl. No.: 11/825,307

(22) Filed: Jul. 5, 2007

(65) Prior Publication Data

US 2008/0021302 A1    Jan. 24, 2008

Related U.S. Application Data

(60) Provisional application No. 60/834,549, filed on Jul. 31, 2006.

(30) Foreign Application Priority Data

Jul. 6, 2006 (DE) .......................... 10 2006 031 937

(51) Int. Cl.
*G06K 9/00* (2006.01)

(52) U.S. Cl. ....................................................... 382/131

(58) Field of Classification Search .................. 382/128, 382/129, 131, 133; 348/130; 128/922, 923; 378/45, 53
See application file for complete search history.

(56) References Cited

U.S. PATENT DOCUMENTS

| 5,289,374 | A | * | 2/1994 | Doi et al. ...................... 600/407 |
| 5,779,634 | A |   | 7/1998 | Ema et al. |
| 6,067,372 | A | * | 5/2000 | Gur et al. ...................... 382/128 |
| 6,292,577 | B1 | * | 9/2001 | Takahashi ...................... 382/128 |
| 2002/0065460 | A1 | * | 5/2002 | Murao ............................ 600/425 |
| 2002/0106119 | A1 | * | 8/2002 | Foran et al. ................... 382/133 |
| 2003/0103663 | A1 | * | 6/2003 | Li et al. ........................... 382/131 |
| 2003/0194121 | A1 |   | 10/2003 | Eberhard et al. |
| 2004/0184644 | A1 | * | 9/2004 | Leichter et al. ............... 382/128 |

(Continued)

FOREIGN PATENT DOCUMENTS

DE     103 06 300 A1    10/2003

OTHER PUBLICATIONS

Ansgar Malich, et al., "Potential MRI Interpretation Model: Differentiation Of Benign from Malignant Breast Masses," *AJR*, vol. 185, pp. 964-970 Oct. 2005.

(Continued)

*Primary Examiner* — Jason M Repko
*Assistant Examiner* — Shervin Nakhjavan
(74) *Attorney, Agent, or Firm* — Patterson Thuente Christensen Pedersen, P.A.

(57) ABSTRACT

A method for quantitative evaluation of an image and/or of an image sequence of tissue or tissue samples for the presence of pathological changes using a database in which there are stored pattern image data and/or pattern image data sequences of tissue patterns that have been identified as predominantly or definitely benign or malignant, and for each sample a weighting factor is stored which indicates whether the pattern occurs predominantly in benign or in malignant tissue changes; it is then analyzed whether any of the pattern images stored in the database are present, within predetermined tolerances, in the image and/or in the sequence of images; based on the sum of the weighting factors of the patterns present, an evaluation factor is formed and made available for further use or output.

17 Claims, 1 Drawing Sheet

U.S. PATENT DOCUMENTS

| | | | | |
|---|---|---|---|---|
| 2004/0264757 A1* | 12/2004 | Bartels | | 382/133 |
| 2006/0018524 A1* | 1/2006 | Suzuki et al. | | 382/128 |
| 2006/0025671 A1* | 2/2006 | Kusunoki | | 600/407 |
| 2006/0059145 A1 | 3/2006 | Henschke et al. | | |
| 2006/0105333 A1* | 5/2006 | Nakamura et al. | | 435/6 |
| 2008/0002873 A1* | 1/2008 | Reeves et al. | | 382/133 |

OTHER PUBLICATIONS

Uwe Fischer, et al., "Breast Carcinoma: Effect of Preoperative Contrast-enhanced MR Imaging on the Therapeutic Approach," *Radiology*, vol. 213, No. 3, pp. 881-888 (1999).

* cited by examiner

METHOD AND DEVICE FOR EVALUATION OF AN IMAGE AND/OR OF A TIME SEQUENCE OF IMAGES OF TISSUE OR TISSUE SAMPLES

RELATED APPLICATIONS

This application claims priority from German Application No. 10 2006 031 937.0, filed Jul. 6, 2006 and from U.S. Provisional Application No. 60/834,549 filed Jul. 31, 2006, the disclosures of which are hereby incorporated by reference.

FIELD OF THE INVENTION

The invention relates to a method and a device for quantitative evaluation of an image and/or of a time sequence of images of tissue or tissue samples for the presence of pathological changes.

BACKGROUND OF THE INVENTION

In medicine, there is currently a multiplicity of different methods of examining tissue for the presence of benign or malignant changes, without having to remove tissue itself in connection with a biopsy that is often very unpleasant for a patient. One of the most frequently employed methods consists in recording and analyzing X-ray images, which usually requires the patient to be injected with a contrast medium. Although X-ray analysis is one of the safest methods, it does expose the patient to a high radiation dose, which may itself, under certain conditions, produce lesions in the tissue by ionization. Therefore, it has been attempted to keep the radiation exposure to a minimum. For example, the dosage of approximately 0.7 Millisievert used in classic mammography is relatively low.

Not least due to the fact that X-rays burden the human organism, other methods of examination have also been developed further over the last few decades, in addition to classic X-ray analysis, such as, for example, ultrasonic analysis, computer tomography, magnetic resonance examinations as well as, based upon the latter, the so-called Magnetic Resonance Imaging (MRI), which used to be referred to also as Magnetic Resonance Tomography (MRT) or Nuclear Magnetic Resonance (NMR). MRI, in particular, has been continuously developed further over the past few years and has proven to be a method excellently suited to represent living organisms. In medicine, MRI is preferably used to image pathological or other physiological changes in tissue.

The analysis of the images—be they X-ray images or MR images—is then usually the responsibility of the physicians in charge. Whether a benign or malignant tissue change is present is assessed by the presence or absence, respectively, of various kinetic or morphological signs or patterns, respectively. In a broader sense, clinical data—such as, for example, serological findings or fever values—can be additionally taken into consideration. Thus, the evaluation of the images and data is strongly dependent on the experience of the physician or physicians. To aggravate the situation, many of the signs or tissue patterns appear in variations, being more pronounced in some patients and less pronounced in others, sometimes not being present at all. This has lead to misdiagnoses time and time again, in particular when analyzing images obtained by the not yet generally established MRI method of examination. For example, in mammography approximately ten to twenty percent of malignant tissue changes are not identified as such. On the other hand, benign tumors are sometimes also mistaken for malignant ones, in the worst case resulting in unjustified removal of a breast in such patients.

Since breast cancer is the second-most frequent cancer-related cause of death in women, there is an ongoing search for ways to avoid such errors as far as possible and/or to reduce the risk of misdiagnoses. In this context, computer aided diagnosis (CAD) plays an important role. Digitized X-ray images, MR images, etc. of tissue are analyzed by image-processing algorithms as to whether certain features, i.e. patterns of signs, can be recognized in the image. If the image-processing software recognizes such features, it will mark them, for example, by highlighting them graphically, thus pointing out these specific regions in the image to the physician looking at the image. It is also the sole responsibility of the physician to decide how the sites found by the image-processing program will be evaluated. Thus, the risk of wrong decisions is not excluded here either, but merely somewhat reduced. Programs capable of learning—such as neuronal networks, for example—are used in an attempt to further reduce these sources of error. In addition, increasingly large databases, such as those of the European MammoGrid project, are being generated so that an ever-increasing set of data is available for CAD. However, the disadvantage still remains that, in the end, a subjective evaluation by the physician decides how the conspicuous phenomena observed by himself and those detected by the program are to be evaluated and whether further steps, such as a biopsy or an operation, are necessary.

SUMMARY OF THE INVENTION

The present invention provides a method for quantitative evaluation of at least one image of a tissue from a patient, including providing a database comprising stored pattern image data of tissue patterns that have been identified as predominantly or definitely benign or malignant, and further comprising a weighting factor for each stored pattern image; analyzing the at least one image to determine whether any of the stored pattern images in the database are present in the at least one image within predetermined tolerances; identifying the weighting factor for each stored pattern image present in the at least one image; and forming an evaluation factor based on the weighting factors of the stored pattern images identified in the at least one image. The at least one image may be part of a series of images from the same tissue. The at least one image may be generated using X-rays or Magnetic Resonance Imaging. The evaluation factor may be formed from the sum of the weighting factors. The weighting factor may be selected to be negative for patterns which occur predominantly in benign tissue changes and to be positive for patterns which occur predominantly in malignant tissue changes. The weighting factor may be determined at least in part on the basis of the ratio of the frequencies with which the pattern occurs in benign tissue changes and in malignant tissue changes.

In another embodiment, the database further comprises combination factors specific for each combination of patterns which substantially appear in combination with other patterns, and, when forming the evaluation factor, the weighting factors for each pattern are combined with the corresponding combination factors for the pattern if the majority of the patterns present in a combination occur in an image.

In another embodiment, the weighting factor used may be the logarithm to the base 10 of the ratio of the frequencies at which the pattern occurs in benign and in malignant tissue changes if the pattern occurs in both types of tissue changes, 3 if the pattern occurs only in malignant tissue changes, and −3 if the pattern occurs only in benign tissue changes.

In another embodiment, the database further comprises additional data selected from the group consisting of clinical and serological data and weighting factors for the additional data, and wherein the weighting factors for the additional data corresponding to additional data determined for or present in the patient when the at least one image was obtained are taken into account when forming the evaluation factor.

In another embodiment, the evaluation factor may be used as a basis for deciding on further measures.

In another embodiment, possible further steps may be suggested on the basis of the evaluation factor.

The present invention also provides for a device for quantitative evaluation of an one or more images of a tissue from a patient for the presence of pathological changes, including a data memory (1) including a database, the database including stored pattern image data from samples of benign tissue and malignant tissue, and further including a weighting factor for each stored pattern image; an analyzing unit (2) in communication with the data memory, the analyzing unit capable of analyzing whether any of the patterns stored in the database are present in an image of a sample of tissue and further capable of forming an evaluation factor based on the weighting factors of the patterns present in an image of the tissue; and an output unit (4) in communication with the analyzing unit for display of the evaluation factor. The one or more images may be part of a series of images from the same tissue. The weighting factor may be negative for patterns which occur predominantly in benign tissue changes and positive for patterns which occur predominantly in malignant tissue changes. The weighting factor may be determined, at least in part, on the ratio of the frequencies with which the patterns occur in benign tissue changes and in malignant tissue changes. The weighting factor is defined as the logarithm to the base 10 of the ratio of the frequencies at which the pattern occurs in benign and in malignant tissue changes if the pattern occurs in both types of tissue changes, is 3 if the pattern occurs only in malignant tissue changes, and is −3 if the pattern occurs only in benign tissue changes.

In another embodiment, the database further comprises combination factors specific for each combination of patterns which substantially appear in combination with other patterns, and, when forming the evaluation factor, the weighting factors for each pattern are combined with the corresponding combination factors for the pattern if the majority of the patterns present in a combination occur in an image.

In another embodiment, the database further comprises additional data selected from the group consisting of clinical and serological data and weighting factors for the additional data, and wherein the weighting factors for the additional data corresponding to additional data determined for or present in the patient when the image was obtained are taken into account when forming the evaluation factor.

In another embodiment, the output unit (4) may display further possible steps on the basis of the evaluation factor and displays them.

DETAILED DESCRIPTION OF THE INVENTION

Figure 1:
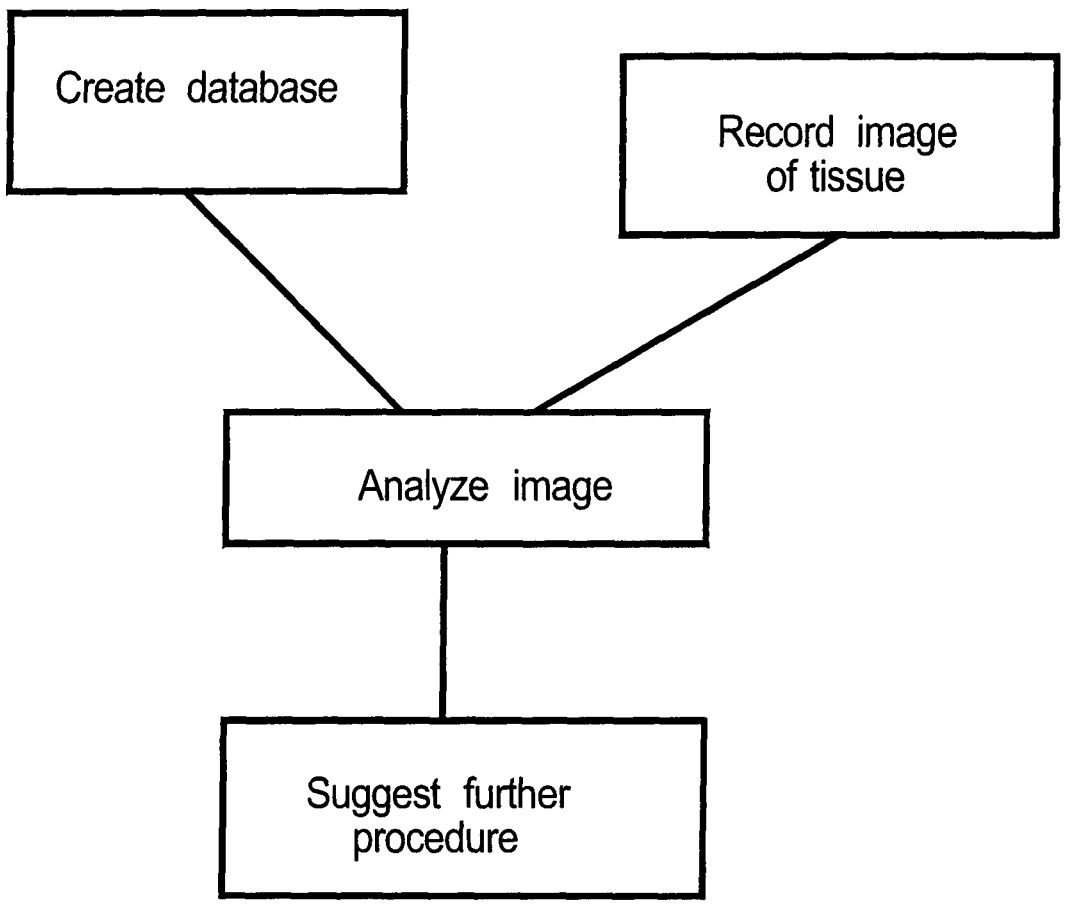
FIG. 1 shows a flow chart of an embodiment of the method of the present invention.

Therefore, it is an object of the present invention to develop a method wherein images of tissue samples and optionally further clinical data are evaluated quantitatively and as objectively as possible.

In a method as described above, this object is achieved by first generating a database, wherein pattern image data and/or time sequences of pattern image data of tissue patterns which have been identified as predominantly or definitely benign or malignant are stored, and by storing for each pattern a weighting factor which indicates whether the pattern occurs predominantly in benign or in malignant tissue changes. Some patterns appear both in benign and in malignant changes. Identification can then be effected both by histopathology and by follow-up control. It is then analyzed whether any of the pattern images stored in the database are present, within predetermined tolerances, in the image and/or in the sequence of images. Based on the sum of the weighting factors of the patterns present, an evaluation factor is then generated and made available for further use and/or output.

Thus, in a first step a databank is generated first. In this database, pattern image data are preferably stored in digital form. In addition, time sequences of pattern image data can also be stored in which, for example, the intensity profile of the signals of a contrast medium over time is recorded. For this purpose, only such pattern image data or sequences of pattern image data, respectively, are stored which correspond to tissue samples or to images of such samples, for which an examination—preferably by histopathology or confirmed by follow-up control—has unambiguously shown whether the tissue change depicted in the image is benign or malignant. This is an essential prerequisite to being able to perform a quantitative evaluation.

The pattern image data may be a sort of average pattern or an idealized pattern which has been constructed from various similar findings in different patients. Each pattern corresponds to a sign which may be present in the afflicted tissue, e.g. the shape of the tissue change, the margin of the tissue change at the transition from changed tissue to unchanged tissue, etc.

The pattern image data or sequences of pattern image data, respectively, are then determined, for example, on the basis of the average appearances of the respective pattern or sign. The graphic/numerical conditions are usually more or less simple ones which are checked by an image-processing program when a new image is being analyzed. Thus, for example, the "sharp margin" finding can be defined as a brightness/darkness change in contrast over a predetermined length substantially perpendicular to the margin, said length preferably being indicated by a unit of length measurement, such as the metric system, and being converted to pixels according to the particular resolution. For instance, with the currently achievable resolutions, a "sharp margin" is present in a transition region of approximately 3 pixels. For another finding, "oval shape", the spatial contour of the margin of the contrast region—which corresponds to the tissue change after injection of a contrast medium—is analyzed. For this purpose, spatial sequences of pattern image data, such as tomographic images, are recorded and analyzed. For example, a suitable pattern image sequence is a similar layer stack, which is accordingly scalable in size, or the indication of ellipsoid coordinates, in which case the image analysis scales the ellipsoid accordingly. This requires certain tolerances to be taken into account, because deviations in shape may occur, however, without implying any other finding. It is also possible to store time sequences of pattern images, for example when the margin is initially sharp, but becomes unsharp and appears washed out in the course of the examination.

In order to be able to make safe statements as to the occurrence of signs or patterns—both terms can be used as synonyms—in benign or malignant tissue changes, a number of images of such signs will be analyzed, which number may range from several few to several ten thousand, depending on how many findings are available. For each pattern, a weighting factor is stored which indicates if and to what extent the pattern appears predominantly in benign or in malignant tissue changes. There are patterns which appear either only in benign or only in malignant tissue changes, but also some which appear in both benign and malignant tissue changes. This is all taken into consideration by the weighting factor. For each pattern image, tolerances are then stored within which deviations are allowable for images being newly examined to still be considered the corresponding sign.

From the total number of findings used as the basis, a weighting factor is determined which indicates whether the pattern or sign appears predominantly in benign tissue changes or predominantly in malignant tissue changes. In this way, an objective and quantifiable statement is possible for the respective sign as to the type of tissue change.

Of course, the database is not a closed structure, but can be continuously supplemented by new findings. Thus, the weighting factors and tolerances are not permanently fixed quantities.

This database, which may be maintained centrally, at a site reserved for this purpose, or distributed at many different locations in the sense of a network, will be made available, preferably in its respectively most current form, to a user—who can certainly also create and maintain said database. Image-processing algorithms are used to analyze whether pattern images stored in the database are present in the image or sequence of images recorded during an examination and then digitized. This involves sequential interrogation of all signs stored as pattern images and analyzing the image or sequence of images to that effect. Since it can be assumed that the signs do not appear in identical form in the various findings, it is necessary to take certain tolerances into account here. These tolerances can be predetermined by the user, but preferably they are determined automatically from the total number of findings.

For those patterns which have been identified by image-processing algorithms as being present in the image to be examined, the weighting factors are then summed up. Thus, only weighting factors of signs actually identified are taken into consideration. In order to keep the error in identification to a minimum, the image-processing algorithms may also be designed, in the sense of neuronal networks, such that they are capable of learning, for example. Finally, an evaluation factor is formed from the sum of the weighting factors, which evaluation factor is made available for further use or is output, for example, on a screen or printer. Further therapeutic measures can then be taken depending on the evaluation factor. In doing so, the recommendation as to what measures should be taken can be made automatically, because only the value of the evaluation factor is decisive. In this way, the method can be used not only on its own, but also to improve or supplement the so-called BIRADS criteria (Breast Imaging Recording and Data System criteria).

The weighting factor is conveniently selected such that it is negative for patterns which appear predominantly in benign tissue changes and positive for patterns which appear predominantly in malignant tissue changes. Of course, an inverse selection of the mathematical signs is also possible, i.e. a positive weighting factor for benign tissue changes and a negative weighting factor for malignant tissue changes—the advantage being that both types of weighting factors differ in their mathematical signs. This makes it particularly easy to perform a quantitative analysis. In this case, the scale for the evaluation factor has its starting point or origin at zero as the central value. Moreover, any other values on the scale are also conceivable, which merely corresponds to shifting of the origin.

The weighting factor is preferably determined by the ratio of the frequencies with which the pattern occurs in benign or malignant tissue changes. In this manner, it is also taken into consideration how many times a pattern or sign was actually recognized while creating the databases. In order to obtain a symmetrical evaluation, the ratio of the frequencies of malignant versus benign tissue changes can be formed. Thus, if this ratio is greater than 1, i.e. if more malignant than benign tissue changes occur, no further processing of the weighting factor occurs. If said ratio is smaller than 1, the inverse is formed and multiplied by −1. In this way, a symmetrical distribution is obtained.

Other distributions are also conceivable. For example, the difference between the number of benign tissue changes and malignant tissue changes, divided by the total number of benign and malignant tissue changes, can also be used as weighting factor. In this case, a scale of weighting factors standardized to 1 is obtained.

For any patterns which substantially appear in combination with other patterns, a combination factor which is specific for each combination is preferably stored in the database. When forming the evaluation factor, the weighting factors of these patterns are respectively linked with the combination factors—for example, by multiplication or by addition—if the majority of the patterns of such a combination occurs. This allows to take the fact into account that certain signs or patterns appear predominantly in combination with other patterns. If such a combination is recognized, it can be weighted more strongly in this way. For example, in mammography a combination of a "skin thickening" pattern or sign—the cutis (corium) of one breast being thicker than that of the other—in connection with a "punched-out" sign—where the signal of the contrast medium strongly increases during an MR examination within a small area of the thickened skin tissue within 90 seconds after injection of the contrast medium, then remains at a plateau or slowly decreases, while the signal increases only slowly in the other areas of the thickened skin—is a strong indicator in favor of an inflammatory carcinoma and against pure mastitis.

In a particularly preferred embodiment of the method, the logarithm to the base 10 of the ratio of frequencies with which the patterns occur in benign and in malignant tissue changes is used as the weighting factor if the pattern appears in both types of tissue change. There are two advantages of selecting this function, which is applied to the ratio of malignant to benign tissue changes: On the one hand, the scale remains easy to overview and, on the other hand, the correct positive or negative mathematical sign is automatically generated. Only if the numerator or the denominator of the ratio equals zero, i.e. if the pattern occurs either only in malignant or only in benign tissue changes, will it be convenient to predetermine values, in this case preferably 3 or −3, respectively. This corresponds to 1000:1 cases, respectively, in which the finding has resulted either in an almost exclusively malignant or exclusively benign tissue change. This selection is arbitrary, i.e. other numbers, such as 4 etc., may also be used, but it should become evident that nearly all findings show the same type of tissue changes, i.e. benign or malignant. Instead of the logarithm to the base 10, other functions may be used as well, e.g. logarithms having other bases, or other suitable functions which automatically result in positive or negative weighting factors as a function of the ratio, with the value 0 being a neutral value. The latter means that such a finding can be called neither benign nor malignant, because it occurs equally frequently. However, the neutral value need not be fixed at zero, but can also be located elsewhere.

In a further preferred embodiment of the method, further clinical and/or serological data with assigned weighting factors and optionally also combination factors are stored in the database in addition to the pattern image data and/or the sequences of pattern image data. As far as data corresponding to the image or sequence of images to be evaluated have been stored, they are compared with the data stored in the database and taken into account when generating the evaluation factor. Of course, this requires that with respect to the image of a tissue sample actually to be examined, corresponding data were determined or present for the patient during recording of the image. The data may be, for example, fever curves, differentiated blood images or serological markers.

The evaluation factor is then referred to as a basis for deciding further measures. A radiologist analyzing a finding according to the cited method steps, will obtain an output evaluation factor of, for example, between −10 and +10—which are arbitrarily fixed limit values here—as a result. Based on the value of said evaluation factor, he can then see what measures seem recommendable, whether no further steps are required, for example, in case of a negative evaluation factor, the interval within which a follow-up examination will be necessary, whether a biopsy is required, or whether therapeutic removal of the tissue should be carried out. The method is suitable for objective evaluation of a finding—if the database is managed correctly—and assists the radiologist in diagnosis.

As an alternative, it may also be envisaged that possible further steps be automatically suggested at the end of the process on the basis of the evaluation factor. This will make interpretation easier for the physician.

The invention also relates to a device—in particular one which is suitable to carry out the method—for quantitative evaluation of an image and/or a sequence of images of tissue or tissue samples for the presence of pathological changes. Such a device comprises a data memory including a database in which pattern image data and/or sequences of pattern image data of tissue patterns which have been identified as predominantly or definitely benign or malignant are stored. Moreover, for each pattern a weighting factor is stored in the database, said weighting factor indicating whether the pattern appears predominantly in benign or in malignant tissue changes. The device further comprises an analyzing unit, wherein (i) it is analyzed whether patterns stored in the database are present in the image and/or in the sequence of images within predetermined tolerances and (ii) an evaluation factor is formed from the sum of the weighting factors of the patterns present and is made available for further use or is output by an output unit.

The data memory and the analyzing unit can be integrated into a commercially available PC. The data memory comprising the database which is structured according to the steps already described above may be the hard disk drive or an external medium, such as a CD or DVD. Even a distributed database managed and maintained by the device is conceivable. In the latter case, the analyzing unit will then access the database via a LAN or the internet, for example. The image of the current finding to be examined is digitally available to the analyzing unit. The analyzing unit uses image-processing algorithms to recognize whether any of the patterns of benign or malignant tissue changes that are stored in the database appear in the image to be examined. Since there is usually no occurrence of identical images, certain tolerances must be given—as described above. The analyzing unit carries out serial or parallel analyses of all patterns stored in the database with respect to their occurrence in the image.

For each pattern, a weighting factor is stored in the database, said factor indicating whether the pattern occurs predominantly or exclusively in benign or malignant tissue changes or, for example, whether it occurs with an even distribution. The weighting factors of those patterns which occur in the image or in the sequence of images are then summed up to yield an evaluation factor. This evaluation factor is then made available for further use, but may also be output to an output unit.

The weighting factor is preferably selected such that it is negative for patterns which occur predominantly in benign tissue changes and positive for patterns which occur predominantly in malignant tissue changes. This makes it easy to decide between benign and malignant tissue changes and facilitates a quantitative evaluation. In this case, the neutral value is zero, i.e. benign and malignant tissue changes occur with the same frequency for the specific pattern. It goes without saying that the weighting factor may also be negative for patterns which appear predominantly in malignant tissue changes and positive for patterns which appear predominantly in benign tissue changes. Other weighting factors, e.g. purely positive or purely negative weighting factors, are also possible, in which case the neutral value is then also positive or negative. However, the advantage of zero as the neutral value is that, although such patterns are recognized, they are not taken into account by the sum and the evaluation, because their respective weighting factor is zero. This makes sense, because an unambiguous decision as to whether the pattern is predominantly present in benign tissue changes or predominantly in malignant tissue changes is obviously not possible.

In order to be able to perform a quantitative evaluation, it is further advantageous if the weighting factor depends on the ratio of the frequency with which the pattern appears in benign versus malignant tissue changes. This allows to take different frequencies into account, i.e. how high the proportion of one type of tissue change is with respect to the proportion of the other type of tissue changes.

The dependence of the weighting factor may relate to the direct relationship of the occurrence of a pattern in benign and malignant tissue changes, i.e. for example the frequency of occurrence in malignant tissue changes relative to the number of occurrences in benign tissue changes, but also to more complicated relationships, such as, for example, the difference between the number of malignant and benign tissue changes, divided by the total number of all tissue changes for the respective signs or patterns, respectively.

In a particularly preferred embodiment of the invention, the weighting factor is defined as the logarithm to the base 10 of the ratio of the frequency with which the patterns appear in benign and in malignant tissue changes if the pattern appears in both types of tissue changes. In this way, it is possible to also take into account relatively large numbers of findings, which are used to generate a pattern image and to determine the respective weighting factor, without such findings dominating in absolute terms. For example, if 999 out of a thousand findings used as a basis for forming the weighting factor have been positive, i.e. correspond to malignant tissue changes, while 9,999 out of a total of 10,000 findings have been positive for another pattern, the absolute frequencies will differ greatly, but the logarithms to the base 10 will be approximately 2 or 3, respectively, so that the differences will not be of great importance here. Therefore, forming logarithms contributes to the objectivity of the result. However, the logarithm cannot be formed if a pattern appears exclusively in benign or in malignant tissue changes. In this case, the weighting factor is preferably 3 if the pattern occurs only in malignant tissue changes and −3 if the pattern appears only in benign tissue changes. These values correspond to frequencies of 1000:1 or 1:1000, respectively, and are thus sufficiently large to document the exclusive occurrence in one or the other type of tissue change; on the other hand, they are not so high that they could dominate the evaluation factor. Of course, values other than 3 and −3 are also conceivable, for example 2.5 and −2.5, etc. It is also possible to use functions other than the logarithm to the base 10, as long as they are suitable for a quantitative evaluation. Thus, for example, logarithms to other bases or the above-mentioned subtraction with standardization by the number of all findings to one pattern or sign can be used as well.

In a further embodiment of the invention, a combination factor which is specific for each combination is stored in the database for such patterns which appear substantially in combination with other patterns. When forming the evaluation factor, the weighting factors are respectively linked with the combination factors, if the majority occurs in such a combination. The storage of combination factors in addition to the weighting factors enables an even more precise analysis and reduces the possibility of errors. It should be noted here once again that the database can be, and usually is, a "living" structure, i.e. that it can be supplemented over time after its completion. For instance, further patterns can be recorded, but it is also possible to merely supplement or newly calculate the weighting factors for existing patterns by incorporating further findings. The same may happen with the combination factors if it turns out that one combination of patterns occurs particularly frequently. The pattern images or sequences of images may also be changed.

In a further embodiment of the invention, further clinical or serological data with their respective weighting factors are also stored in the database in addition to the pattern images and the sequences of pattern images. If corresponding data for the tissue or the tissue sample whose image is being evaluated are stored in the data memory in addition to the image, they will be compared by the analyzing unit with the clinical and/or serological data stored in the database and will be taken into account accordingly by the weighting factors when forming the evaluation factor. Using such data, the precision of the method can be further increased.

In a further embodiment of the invention, the output unit determines further possible steps on the basis of the evaluation factor and displays them. Such display may be effected on a screen, but also printed out on paper. For example, the radiologist in charge can then take further steps on the basis of the proposal, such as initiate a longer phase of observation, perform a biopsy or, in the best of cases, send the patient home without a pathological finding.

Whereas the device according to the invention, which is suitable to carry out the method of the invention, cannot replace diagnosis, it can nevertheless objectively provide the physician in charge with suggestions as to the further procedure by quantitative analysis in a very safe manner. In particular, younger physicians, who naturally do not have great experience with respect to the manifold variations in the appearance of the same pattern in tissue changes or are not yet familiar with some signs, can be assisted in this way, because all kinds of signs are interrogated and the error of an inadvertent discovery or oversight is eliminated. However, even more experienced physicians may thus be kept from misdiagnosis under certain circumstances and may be incited to carry out a further in-depth examination.

The invention will be explained in more detail below with reference to an exemplary embodiment. In the pertinent drawings:

FIG. 1 shows a flow chart of the method and

Figure 2:
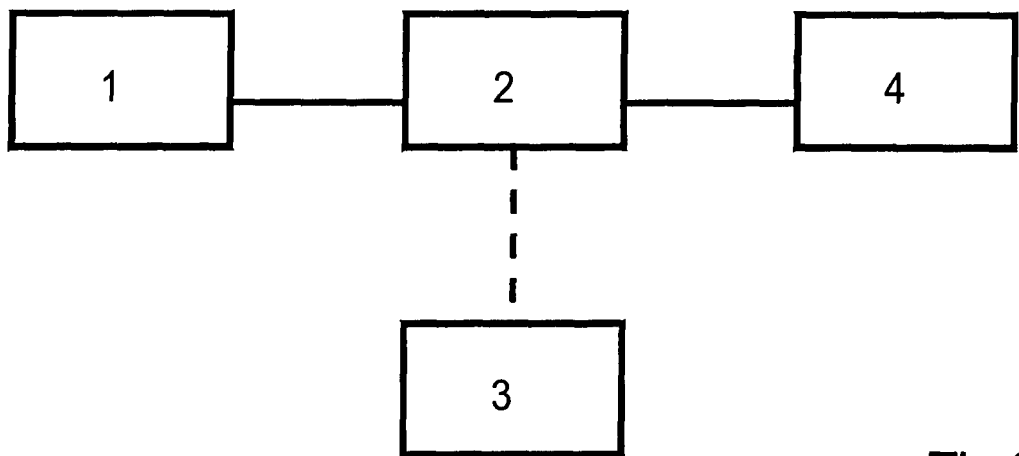
FIG. 2 shows elements of a device according to an embodiment of the present invention.

FIG. 2 shows a device using which the method can be carried out.

First of all, FIG. 1 shows the usual sequence of the method according to the invention. In a first basic step, a database is initially created. This is based on sufficiently reliable results of examinations of tissue changes, for example in breast tissue, on a number N of patients. These patients were preferably examined under the same conditions. This means, for example, the same dose in X-ray imaging or the same magnetic field strength in MR examinations. Of course, this is not stringently required, but it does facilitate the subsequent analysis of images. In this case, "sufficiently reliable" means that, among this number N of patients, tissue samples are either examined pathologically, so as to obtain a histologically unambiguous finding, or that a follow-up control—which is appropriate especially in case of benign changes—allows a sufficiently reliable identification or characterization, respectively, of the tissue change. The recorded images of the suspicious tissue in the patients are then either digitized directly and stored as pattern image data in the database; in addition, the images can also be evaluated first by experienced radiologists in a blinded study so as to increase the precision with respect to the presence of signs or patterns which have turned out, over time, to be indicators of benign or malignant tissue changes. These signs or patterns include, for example, the temporal and spatial profile of the signal of a contrast medium injected prior to the start of recording. As regards the spatial profile, for example, the profile of the margin separating the region from which the signals come from the region from which no signals come is of importance. Whether said profile has an oval, round or irregular shape—each of the aforementioned appearances forms its own pattern or sign. Apart from the aforementioned signs, there are also a multiplicity of further patterns, which occur more or less frequently, sometimes only in combination with other signs. All of these signs or patterns are included in the database. Therefore, tolerances are also stored for each image data set, which result from the deviations observed in each finding. In this manner, it is also possible to consider different recording parameters. However, it is preferred that different pattern image datasets be created for different recording parameters, even if they concern the same pattern or sign.

A weighting factor is then determined for each pattern, which factor indicates whether the pattern appears predominantly in benign or malignant tissue changes, and is then stored in the database, where it is assigned to the corresponding pattern image dataset or pattern image sequence dataset. The weighting factors are preferably used as logarithm to the base 10 of the quotient resulting from the number of malignant tissue changes relative to the number of benign tissue changes to form a pattern image dataset, if the pattern is present both in benign and in malignant tissue changes. If the pattern is present only in benign tissue changes, the weighting factor is set to a value of −3, which corresponds to a ratio of 1:1000; in the case of purely malignant tissue changes with respect to a sign, the weighting factor is set to 3, which corresponds to a ratio of 1000:1.

In doing so, the database may be maintained locally, i.e. within the hospital or the doctor's office, or globally, i.e. in connection with several clinics, for example. Moreover, the database can be continuously expanded, for example if new findings for a pattern are added or if new patterns or signs are discovered.

The next step may then be temporally independent of the provision of the database and only requires the presence of the database. This involves recording an image of suspicious tissue. The image should then be present in digital form as well. An analysis is then effected as to whether pattern image data or pattern image data sequences stored in the database are present in the image and/or image sequence within the given tolerances. In addition, a comparison with further, clinical and serological data may also be effected. The analysis may be effected by means of adjusted image-processing algorithms existing in the prior art. In the image analysis, basically all signs or patterns which are present as pattern image data are examined as to whether they appear in the images or image sequences to be analyzed. The comparison may be limited to comparing only with such pattern images that have been recorded using the same or at least similar recording parameters.

In the final step, the evaluation factor is formed. For this purpose, the weighting factors of the present patterns are summed up. The easiest manner of forming the evaluation factor in mathematical numerical terms is to provide all weighting factors with a mathematical sign factor $s_k$ which indicates whether a pattern k is present in the analyzed image ($s_k=1$) or does not appear therein ($s_k=0$). If the weighting factor for a pattern k is designated as $w_k$, the evaluation factor B, in this case, will result as $$B = \sum_{k=1}^{K} s_k w_k.$$

K is the total number of patterns or signs, respectively, stored in the database and used for analysis. A combination factor may also be taken into account by $w_k$.

At the end of the analysis, the evaluation factor can then be output directly. It is advantageous here, in particular for examination personnel not having too much experience, to make a suggestion directly as to the further procedure, in addition or instead of the evaluation factor. Of course, such suggestion cannot replace a full diagnosis with histopathological examination. For example, a strongly negative evaluation factor could be combined with the statement that no further steps are required. A slightly negative or slightly positive evaluation factor could be combined with the statement that long-term or short-term supervision and a follow-up examination should take place. Higher evaluation factors can be combined with the statement that a biopsy is recommended or that therapeutic removal of the tissue appears necessary.

FIG. 2 shows a device using which the method according to the invention can be carried out. This device comprises, first of all, a data memory 1, which contains a database—created and maintained as above—in which pattern image data and/or pattern image data sequences are stored of tissue patterns identified as definitely or predominantly benign or malignant by histopathology or by means of follow-up control. In addition, a weighting factor is stored for each tissue pattern, which factor indicates whether the pattern appears predominantly in benign or malignant tissue changes. The data memory 1 is connected to an analyzing unit 2, preferably bidirectionally, so that database maintenance, for example, can take place via the analyzing unit 2. The data memory 1 and the analyzing unit 2 need not be located in each other's immediate vicinity, but can also be spatially far apart from each other, for example if the database in the data memory 1 is maintained at a central site, and all clinics or doctor's offices access it.

It is analyzed in the analyzing unit 2 whether any of the pattern images or pattern image sequences stored in the database are present, within predetermined tolerances, in the image and/or in the sequence of images. The analyzing unit 2 may optionally be connected to a recording unit 3, which may be part of the examining equipment. The recorded image that is to be analyzed is preferably digitized and transmitted to the analyzing unit 2. At the end of the image analysis, an evaluation factor is formed from the sum of the weighting factors of the patterns identified in the image. According to the value of the evaluation factor, suggestions as to the further procedure are displayed, as already described above, on an output unit 4, which is also connected to the analyzing unit 2.

The system according to the invention for evaluation of images with tissue changes provides an important contribution to the further development of computer-assisted diagnosis, due to images being quantitatively evaluated with high objectivity, because they are examined for the presence of the sum of all known and stored signs and/or patterns. The evaluation is based on the systematic analysis of all known signs with corresponding weighting. This allows to assist, in particular, radiologists having less experience in examination. Moreover, if the database is maintained such that only images of like quality are taken into account, the suggested system of evaluation can serve as a basis for standardization of diagnosis and treatment.

The invention claimed is:

1. A method for quantitative evaluation of at least one image of a tissue from a patient, comprising:
    providing a database comprising stored pattern image data of tissue patterns that have been identified as predominantly or definitely benign or malignant, and further comprising a weighting factor for each stored pattern image, wherein the weighting factor indicates whether the pattern appears predominately in benign tissue changes or malignant tissue changes, the weighting factor is determined at least in part on the basis of the ratio of the frequencies with which the pattern occurs in benign tissue changes and in malignant tissue changes, and the weighting factors for patterns appearing predominantly in benign tissue changes and the weighting factors for patterns appearing predominantly in malignant tissue changes differ in their respective mathematical signs;
    analyzing the at least one image to determine whether any of the stored pattern images in the database are present in the at least one image within predetermined tolerances;
    identifying the weighting factor for each stored pattern image present in the at least one image;
    forming an evaluation factor from the sum of the weighting factors of the stored pattern images identified in the at least one image; and
    using the evaluation factor as a basis for deciding on further measures.

2. The method as claimed in claim 1, wherein the at least one image is part of a series of images from the same tissue.

3. The method as claimed in claim 1, wherein the at least one image is generated using X-rays or Magnetic Resonance Imaging.

4. The method as claimed in claim 1, wherein the evaluation factor is formed from the sum of the weighting factors.

5. The method as claimed in claim 1, wherein the weighting factor is selected to be negative for patterns which occur predominantly in benign tissue changes and to be positive for patterns which occur predominantly in malignant tissue changes.

6. The method as claimed in claim 1, wherein the database further comprises combination factors specific for each combination of patterns which substantially appear in combination with other patterns, and, when forming the evaluation factor, the weighting factors for each pattern are combined with the corresponding combination factors for the pattern if the majority of the patterns present in a combination occur in an image.

7. The method as claimed in claim 1, wherein the weighting factor used is the logarithm to the base 10 of the ratio of the frequencies at which the pattern occurs in benign and in malignant tissue changes if the pattern occurs in both types of tissue changes, 3 if the pattern occurs only in malignant tissue changes, and −3 if the pattern occurs only in benign tissue changes.

8. The method as claimed in claim 1, wherein the database further comprises additional data selected from the group consisting of clinical and serological data and weighting factors for the additional data, and wherein the weighting factors for the additional data corresponding to additional data determined for or present in the patient when the at least one image was obtained are taken into account when forming the evaluation factor.

9. The method as claimed in claim 1, wherein possible further steps are suggested on the basis of the evaluation factor.

10. A device for quantitative evaluation of an one or more images of a tissue from a patient for the presence of pathological changes, comprising
a data memory comprising a database, the database comprising stored pattern image data from samples of benign tissue and malignant tissue, and further comprising a weighting factor for each stored pattern image, wherein the weighting factor indicates whether the pattern appears predominately in benign tissue changes or malignant tissue changes, the weighting factor is determined at least in part on the basis of the ratio of the frequencies with which the pattern occurs in benign tissue changes and in malignant tissue changes, and the weighting factors for patterns appearing predominantly in benign tissue changes and the weighting factors for patterns appearing predominantly in malignant tissue changes differ in their respective mathematical signs;
an analyzing unit in communication with the data memory, the analyzing unit capable of analyzing whether any of the patterns stored in the database are present in an image of a sample of tissue and further capable of forming an evaluation factor from the sum of the weighting factors of the patterns present in an image of the tissue; and
an output unit in communication with the analyzing unit for display of the evaluation factor.

11. The device as claimed in claim 10, wherein the one or more images are part of a series of images from the same tissue.

12. The device as claimed in claim 10, wherein the weighting factor is negative for patterns which occur predominantly in benign tissue changes and positive for patterns which occur predominantly in malignant tissue changes.

13. The device as claimed in claim 10, wherein the weighting factor is determined, at least in part, on the ratio of the frequencies with which the patterns occur in benign tissue changes and in malignant tissue changes.

14. The device as claimed in claim 10, wherein the weighting factor is defined as the logarithm to the base 10 of the ratio of the frequencies at which the pattern occurs in benign and in malignant tissue changes if the pattern occurs in both types of tissue changes, is 3 if the pattern occurs only in malignant tissue changes, and is −3 if the pattern occurs only in benign tissue changes.

15. The device as claimed in claim 10, wherein the database further comprises combination factors specific for each combination of patterns which substantially appear in combination with other patterns, and, when forming the evaluation factor, the weighting factors for each pattern are combined with the corresponding combination factors for the pattern if the majority of the patterns present in a combination occur in an image.

16. The device as claimed in claim 10, wherein the database further comprises additional data selected from the group consisting of clinical and serological data and weighting factors for the additional data, and wherein the weighting factors for the additional data corresponding to additional data determined for or present in the patient when the image was obtained are taken into account when forming the evaluation factor.

17. The device as claimed in claim 10, wherein the output unit (4) displays further possible steps on the basis of the evaluation factor and displays them.

* * * * *